(12) United States Patent
O'Reilly

(10) Patent No.: US 8,670,811 B2
(45) Date of Patent: Mar. 11, 2014

(54) PULSE OXIMETRY SYSTEM FOR ADJUSTING MEDICAL VENTILATION

(75) Inventor: Michael O'Reilly, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 290 days.

(21) Appl. No.: 12/824,087

(22) Filed: Jun. 25, 2010

(65) Prior Publication Data

US 2010/0331639 A1 Dec. 30, 2010

Related U.S. Application Data

(60) Provisional application No. 61/222,087, filed on Jun. 30, 2009.

(51) Int. Cl.
*A61B 5/00* (2006.01)

(52) U.S. Cl.
USPC .......................................................... 600/323

(58) Field of Classification Search
USPC ..................................... 600/323; 128/204.23
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,278,627 A | 1/1994 | Aoyagi et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,680,857 A * | 10/1997 | Pelikan et al. | 600/323 |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |

(Continued)

*Primary Examiner* — Clayton E Laballe
*Assistant Examiner* — Noam Reisner
(74) *Attorney, Agent, or Firm* — Knobbe Martens Olson & Bear LLP

(57) ABSTRACT

A physiological monitoring system can include a physiological monitor having one or more processors that can derive oxygen saturation values from a patient. The oxygen saturation values can correspond to values of oxygen saturation in blood at a tissue site of the patient. The physiological monitor can output an indication of amplitude of the differences per respiratory cycle in the oxygen saturation values.

17 Claims, 5 Drawing Sheets

(56) References Cited

U.S. PATENT DOCUMENTS

| | | |
|---|---|---|
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,008,380 B1 | 3/2006 | Rees et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |

(56) References Cited

U.S. PATENT DOCUMENTS

| | | | |
|---|---|---|---|
| D554,263 S | 10/2007 | Al-Ali | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| 7,328,053 B1 | 2/2008 | Diab et al. | |
| 7,332,784 B2 | 2/2008 | Mills et al. | |
| 7,340,287 B2 | 3/2008 | Mason et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,355,512 B1 | 4/2008 | Al-Ali | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,373,194 B2 | 5/2008 | Weber et al. | |
| 7,376,453 B1 | 5/2008 | Diab et al. | |
| 7,377,794 B2 | 5/2008 | Al Ali et al. | |
| 7,377,899 B2 | 5/2008 | Weber et al. | |
| 7,383,070 B2 | 6/2008 | Diab et al. | |
| 7,415,297 B2 | 8/2008 | Al-Ali et al. | |
| 7,428,432 B2 | 9/2008 | Ali et al. | |
| 7,438,683 B2 | 10/2008 | Al-Ali et al. | |
| 7,440,787 B2 | 10/2008 | Diab | |
| 7,454,240 B2 | 11/2008 | Diab et al. | |
| 7,467,002 B2 | 12/2008 | Weber et al. | |
| 7,469,157 B2 | 12/2008 | Diab et al. | |
| 7,471,969 B2 | 12/2008 | Diab et al. | |
| 7,471,971 B2 | 12/2008 | Diab et al. | |
| 7,483,729 B2 | 1/2009 | Al-Ali et al. | |
| 7,483,730 B2 | 1/2009 | Diab et al. | |
| 7,489,958 B2 | 2/2009 | Diab et al. | |
| 7,496,391 B2 | 2/2009 | Diab et al. | |
| 7,496,393 B2 | 2/2009 | Diab et al. | |
| D587,657 S | 3/2009 | Al-Ali et al. | |
| 7,499,741 B2 | 3/2009 | Diab et al. | |
| 7,499,835 B2 | 3/2009 | Weber et al. | |
| 7,500,950 B2 | 3/2009 | Al-Ali et al. | |
| 7,509,154 B2 | 3/2009 | Diab et al. | |
| 7,509,494 B2 | 3/2009 | Al-Ali | |
| 7,510,849 B2 | 3/2009 | Schurman et al. | |
| 7,526,328 B2 | 4/2009 | Diab et al. | |
| 7,530,942 B1 | 5/2009 | Diab | |
| 7,530,949 B2 | 5/2009 | Al Ali et al. | |
| 7,530,955 B2 | 5/2009 | Diab et al. | |
| 7,563,110 B2 | 7/2009 | Al-Ali et al. | |
| 7,596,398 B2 | 9/2009 | Al-Ali et al. | |
| 7,618,375 B2 | 11/2009 | Flaherty | |
| D606,659 S | 12/2009 | Kiani et al. | |
| 7,647,083 B2 | 1/2010 | Al-Ali et al. | |
| D609,193 S | 2/2010 | Al-Ali et al. | |
| D614,305 S | 4/2010 | Al-Ali et al. | |
| RE41,317 E | 5/2010 | Parker | |
| 2004/0116784 A1* | 6/2004 | Gavish | 600/300 |
| 2006/0281983 A1* | 12/2006 | Al-Ali et al. | 600/323 |
| 2008/0188760 A1* | 8/2008 | Al-Ali et al. | 600/507 |

\* cited by examiner

PULSE OXIMETRY SYSTEM FOR ADJUSTING MEDICAL VENTILATION

REFERENCE TO RELATED APPLICATIONS

This application claims priority benefit under 35 U.S.C. §119(e) of U.S. Provisional Application No. 61/222,087 filed Jun. 30, 2009, entitled "Pulse Oximetry System for Adjusting Medical Ventilation." The present application incorporates the disclosure of the foregoing application herein by reference in its entirety.

FIELD OF INVENTION

The present disclosure relates to patient monitors and medical ventilation.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a patient's physiological parameters. Physiological parameters include, for example, blood pressure, respiratory rate, oxygen saturation ($SpO_2$) level, other blood constitutions and combinations of constitutions, and pulse, among others. Clinicians, including doctors, nurses, and certain other caregiver personnel use the physiological parameters obtained from the patient to diagnose illnesses and to prescribe treatments. Clinicians can also use the physiological parameters to monitor a patient during various clinical situations to determine whether to increase the level of care given to the patient. Various patient monitoring devices are commercially available from Masimo Corporation ("Masimo") of Irvine, Calif.

SUMMARY

The present disclosure provides for the measurement, display and analysis of oxygenation saturation during the respiratory cycle. This advantageously allows a physician to monitor the amplitude of the difference between a low and high value in the patient's blood oxygen saturation over a respiration cycle. This advantageously allows a physician to determine whether adjustment of the ventilation parameters is desired.

In one embodiment, disclosed is a noninvasive method of analyzing the amplitude of the differences in oxygen saturation of a patient, the method comprising deriving oxygen saturation values from a patient the oxygen saturation values reflecting oxygenation saturation of the a tissue site and outputting an indication of the amplitude of the differences in the oxygen saturation values per respiratory cycle. The amplitude of the difference in the oxygen saturation may reflect a health status of the lungs of the patient. In an embodiment, the amplitude of the differences tracks the respiratory cycle.

The outputting of the indication of the amplitude of the amplitude of the differences may comprise outputting a graph of oxygen saturation values, or outputting a percentage value of variability. In one embodiment, a method is disclosed that determines whether the amplitude of the differences in oxygen saturation values is above a threshold value. In some embodiments, an alarm is generated in response to the variability being above the threshold value.

In some embodiments, control signals are provided to a ventilator responsive to the amplitude of the differences in oxygen saturation. The control signal may increase or decrease an $FiO_2$, amount delivered by the ventilator to the patient. In some embodiments, the $FiO_2$ amount is increased or decreased to keep the patient's oxygen saturation values on a steep part of a $SpO_2$ versus $FiO_2$ curve of the patient.

Also disclosed is a physiological monitoring system, the system comprising a physiological monitor with one or more processors configured to derive oxygen saturation values from a patient the oxygen saturation values corresponding to values of oxygen saturation in blood at a tissue site, and output an indication of the amplitude of the differences per respiratory cycle in the oxygen saturation values. The amplitude of the differences in the oxygen saturation may reflect a health status of the lungs of the patient or track a respiratory cycle of the patient.

In some embodiments the physiological monitor is further configured to output the indication of amplitude of the differences by at least outputting a graph of oxygen saturation values or a percentage value of amplitude of the differences. The monitor may be configured to determine whether the amplitude of the differences in the oxygen saturation is above a threshold value. The physiological monitor may be further configured to generate an alarm in response to the amplitude of the differences being above the threshold value. In some embodiments, the physiological monitor may be further configured to derive the oxygen saturation values from a physiological signal obtained by a noninvasive optical sensor.

DETAILED DESCRIPTION

Medical ventilators are often used to assist patients with breathing. Ventilators can deliver oxygen into a patient's lungs and control the removal of carbon dioxide. Ventilators typically include different settings or parameters that can be adjusted to provide an appropriate amount of ventilation to a patient. These parameters might include, for example, pressure, volume of air provided, and respiration rate. An artisan will recognize from the disclosure herein a wide variety of commercially available ventilator systems, other ventilator systems, and characteristics of ventilator systems known to the ventilator device community.

Significant damage can occur to the lungs, and in particular, to the alveoli structures in the lungs, when ventilation parameters are not appropriate. For instance, too much volume can cause the delicate alveoli to stretch and then collapse, causing injury to the lungs and pulmonary failure. To avoid this problem, clinicians adjust the ventilation to reduce the distention and collapse the alveoli to prevent lung injury. Thus, a clinician often tries to balance the several ventilation parameters to avoid serious lung damage while providing sufficient air to a patient but not have the alveoli collapse.

This disclosure describes certain systems and methods for indicating when clinicians should consider adjusting ventilation parameters of a medical ventilator. In certain embodiments, a physiological monitor measures at least a patient's blood oxygen saturation noninvasively. The physiological monitor may provide an indication of the amplitude of the difference between a low and high value in the patient's blood oxygen saturation over a predetermined time and/or respiration cycle. A clinician may infer from the indication of the amplitude of the difference of oxygen saturation measurements that adjustment of the ventilation parameters is desired. In response to the clinician adjusting the parameters properly, the amplitude of the differences of the oxygen saturation may advantageously decrease, thereby stabilizing the patient's oxygen and finding the foregoing balance that can ensure proper lung ventilator interactions. The amplitude indication can therefore provide the clinician with feedback that can help advantageously reduce the risk of lung failure.

Figure 1:
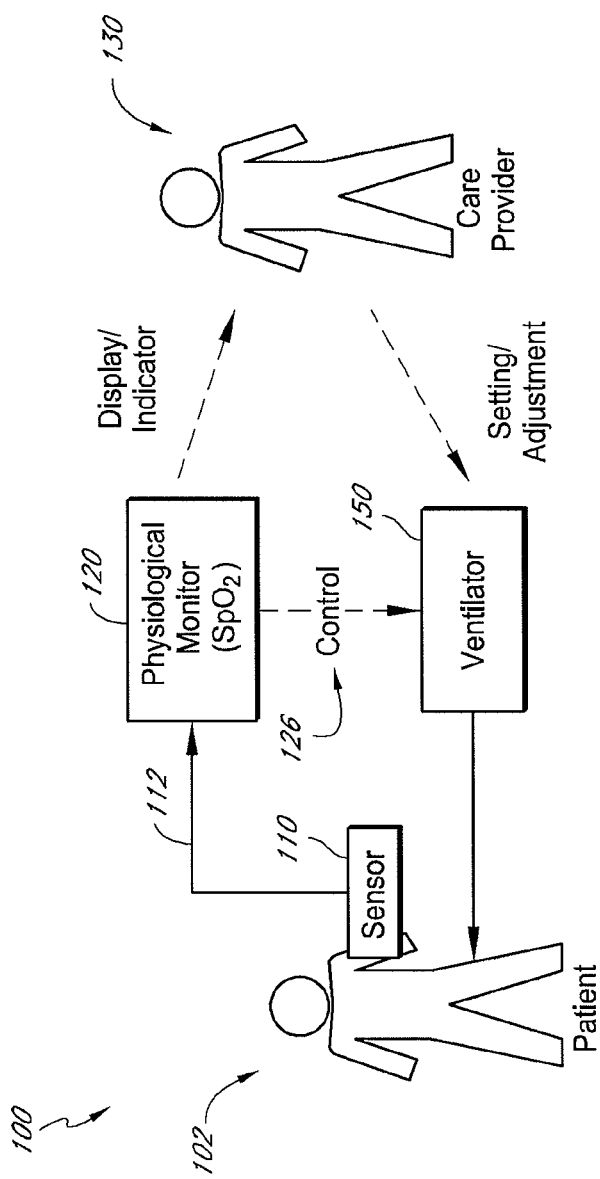
FIG. 1 illustrates an embodiment of a patient monitoring system for determining oxygen saturation variability.

FIG. 1 illustrates an example patient monitoring system 100. The patient monitoring system 100 may be used to monitor the health status of a patient, including the status of a patient's blood oxygen saturation, although many other parameters may also be monitored. The patient monitoring system 100 can assist a care provider 130 with determining when to adjust ventilator parameters to reduce the risk of lung damage to a patient 102.

In the depicted embodiment, the patient 102 is receiving breathing assistance from a ventilator 150. The patient 102 could receive air from the ventilator 150 through a face mask, intubation tube, or the like. The ventilator 150 may include controls that allow adjustment of ventilation parameters such as inspiratory pressure, air volume, desired respiratory rate, end-expiratory pressure (PEEP), inspiration: expiration ratio (I:E), Fraction of Inspired Oxygen ($FiO_2$), tidal volume (TV), and the like.

The patient 102 is also being monitored by a noninvasive sensor 110. The sensor 110 can be an optical sensor that irradiates a tissue site of the patient 102 with one or more wavelengths of optical radiation. The sensor 110 can detect radiation transmitted through the tissue site of the patient and provide an absorption signal 112 to a physiological monitor 120.

The physiological monitor 120 may have one or more processors that can analyze the absorption signal 112 to determine one or more blood constituents of the patient 102, such as blood oxygen saturation. The physiological monitor 120 can measure oxygen saturation values. The oxygen saturation values measured by the physiological monitor 120 can be somewhat averaged over a respiratory cycle. In other words, in certain embodiments, a shorter averaging time is applied to the oxygen saturation values so as to obtain oxygen saturation values that more closely track actual or instantaneous oxygen saturation over a respiratory cycle. In other embodiments, the physiological monitor 120 does not apply any averaging to the oxygen saturation values.

Advantageously, in certain embodiments, the physiological monitor 120 detects the amplitude of the difference between the highest and lowest oxygen saturation measurements over a set amount of time. Increases and decreases in the oxygen saturation can track or approximately track the patient's 102 respiratory cycle (e.g., a cycle of recruitment and collapse of alveoli). The magnitude of the differences in the oxygen saturation values over time can reflect the degree of recruitment and collapse of alveoli in the respiratory cycle. The physiological monitor 120 can calculate the amplitude of the difference of the lowest and highest values from the set of values included in a window defined by the peak-to-peak oxygen saturation amplitudes with each respiratory cycle or with a selection of respiratory cycles.

In some patients, such as in a ventilated patient 102, high amplitude of differences of oxygen saturation over each respiratory cycle can reflect overextension of the alveoli of the lungs. This overextension may be caused by too much air pressure or volume followed by too little air pressure or volume. A normal or healthy amplitude of the differences between oxygen saturation high and low values may be, for example, about 2% to about 3% or less, about 1% to about 2% or less, or the like. An amplitude of differences between high and low values that can reflect a risk of lung damage might be greater than about 2% to about 3%, greater than about 4% to about 5%, or the like. Normal and abnormal ranges of the amplitude of oxygen saturation differences can depend on the age of the patient (e.g., neonate versus child versus adult), the gender of the patient, comorbidity of the patient, and the like. When the foregoing measurements show greater amplitude of differences than discussed, particularly when the increases and decreases in oxygen saturation tracks or substantially tracks each respiratory cycle, then ventilation adjustment may advantageously reduce the amplitude of the difference between the high and low values over a respiratory cycle.

The physiological monitor 120 can advantageously provide an indication of the amplitude of the difference in oxygen saturation over a respiratory cycles for presentation to the care provider 130. For example, the physiological monitor 120 can display oxygen saturation values, an oxygen saturation graph, an amplitude of the differences indicator, combinations of the same, or the like. In some implementations, the physiological monitor 120 outputs an audio and/or visual alarm that alerts the care provider 130 to high amplitude of differences in oxygen saturation high and low values over respiratory cycles. Example monitor 120 displays are described below with respect to FIGS. 2 and 3.

The care provider 130 can use the information provided by the physiological monitor 120 to determine whether to adjust settings 142 of the ventilator 150. For example, the care provider 130 could adjust one or more of air pressure, air volume, respiratory rate, end-expiratory pressure (PEEP), inspiration: expiration ratio (I:E), $FiO_2$, tidal volume (TV), and the like. In one scenario, if the amplitude of the differences between the high and low values over a respiratory cycle is too high, the care provider 130 might reduce the air pressure and/or air volume provided by the ventilator 150 while increasing the respiratory rate to provide the patient 102 with sufficient air. Adjusting the ventilation parameters could cause the amplitude of the differences in the oxygen saturation to decrease with each respiratory cycle from the previous high amplitude. The physiological monitor 120 could output an indication of the decreased amplitude. The care provider 130 could continue to adjust the ventilation parameters until the physiological monitor 120 reflects a reduced or minimized amplitude of the differences.

In alternative embodiments, the physiological monitor 120 can provide a control signal 126 directly to the ventilator 150 based at least partly on the detected amplitude of the differences in oxygen saturation. The control signal 126 can cause the ventilator 150 to automatically adjust one or more of the ventilation parameters described above. Alternatively, the control signal 126 can cause the ventilator 150 to alarm or to display a recommendation to adjust ventilation parameters on a display of the ventilator 150, as opposed to fully controlling the ventilator 150. The physiological monitor 120 can generate this control signal 126 instead of or in addition to providing a saturation value, oxygen saturation graph, indicator, alarm, or the like.

Figure 2:
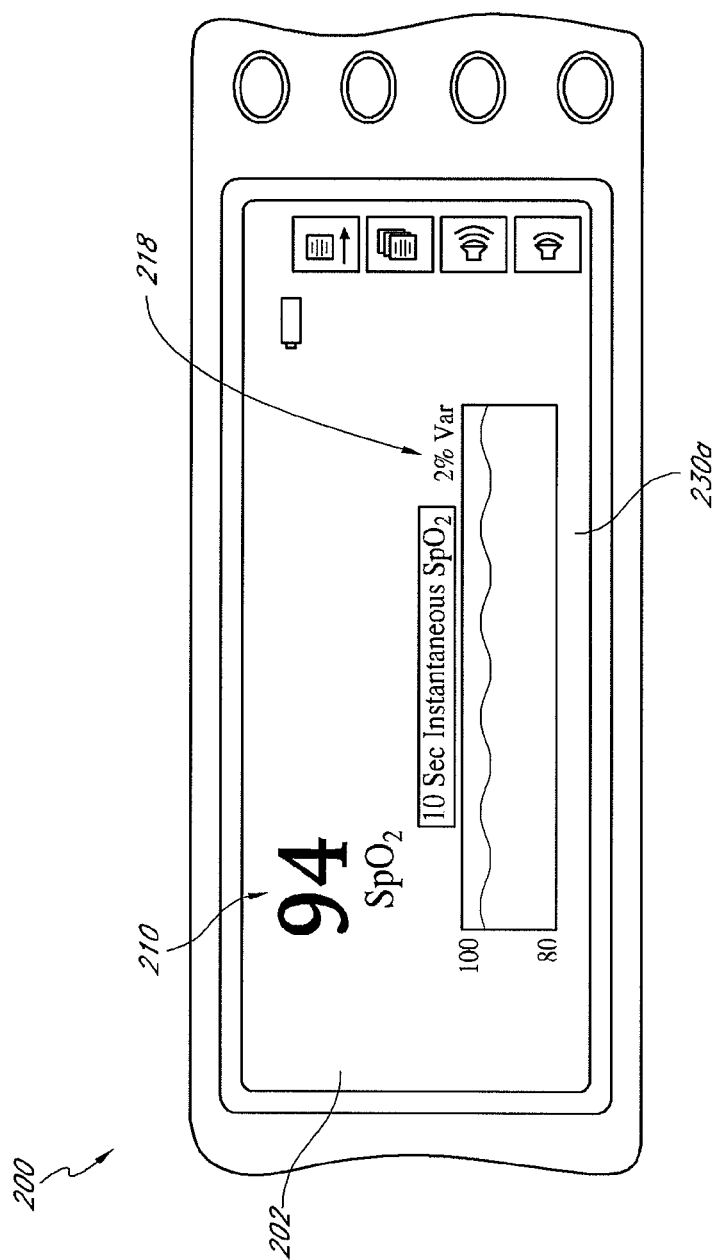
FIGS. 2 and 3 illustrate example physiological monitor display providing indications of oxygen saturation variability.

FIG. 2 illustrates an example physiological monitor 200 having a display 202. The display 202 includes parameter data for oxygen saturation, including a measured value of $SpO_2$ 210, an $SpO_2$ graph 230a, and an amplitude of the differences indicator 218. The measured value 210 of SpO$_2$ can be an SpO$_2$ value that is partially averaged over a respiratory cycle or not averaged at all. The SpO$_2$ graph 230*a* depicts these SpO$_2$ values over several respiratory cycles. In the example display 202 shown, the SpO$_2$ graph 230*a* exemplifies a normal amplitude of differences over a respiratory cycle. A present amplitude of differences of 2% is shown by the amplitude indicator 218.

Figure 3:
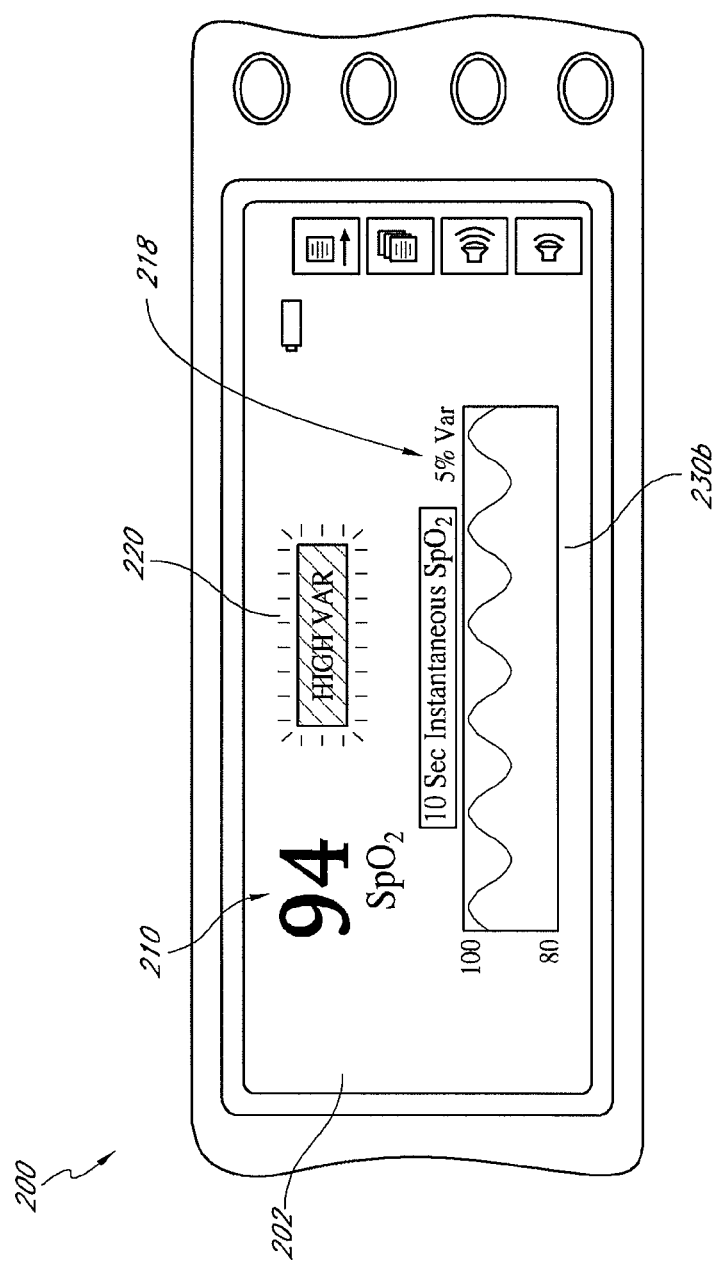

FIG. 3 illustrates the example physiological monitor 200 of FIG. 2 when high amplitude of differences between oxygen saturation values occurs over respiratory cycles. As shown, the SpO$_2$ graph 230*b* depicts a higher amplitude of differences in the oxygen saturation, and the amplitude indicator 218 indicates that 5% amplitude of differences is present.

A visual oxygen saturation alarm 220 is also shown. The oxygen saturation alarm 220 includes text that indicates that the oxygen saturation amplitude of differences is high. The oxygen saturation alarm 220 may be displayed, for example, when a patient's oxygen saturation amplitude of differences increases above a threshold value. The visual oxygen saturation alarm 220 may be accompanied by or be replaced by an audio alarm in certain embodiments. The visual oxygen saturation alarm 220 and/or audible alarm may indicate to a care provider that adjustment to ventilation parameters is desired.

The example display 202 depicted in FIGS. 2 and 3 are merely illustrative. Other displays can include fewer than all the features shown in the display 202. For instance, the alarm 220 and amplitude indicator 218 may be omitted, and a care provider could make a variability determination solely based on the SpO$_2$ graph 230. Alternatively, the SpO$_2$ graph 230 could be omitted, and the alarm 220 and/or indicator 218 may be displayed instead. Many other variations may be provided in other implementations.

Figure 4:
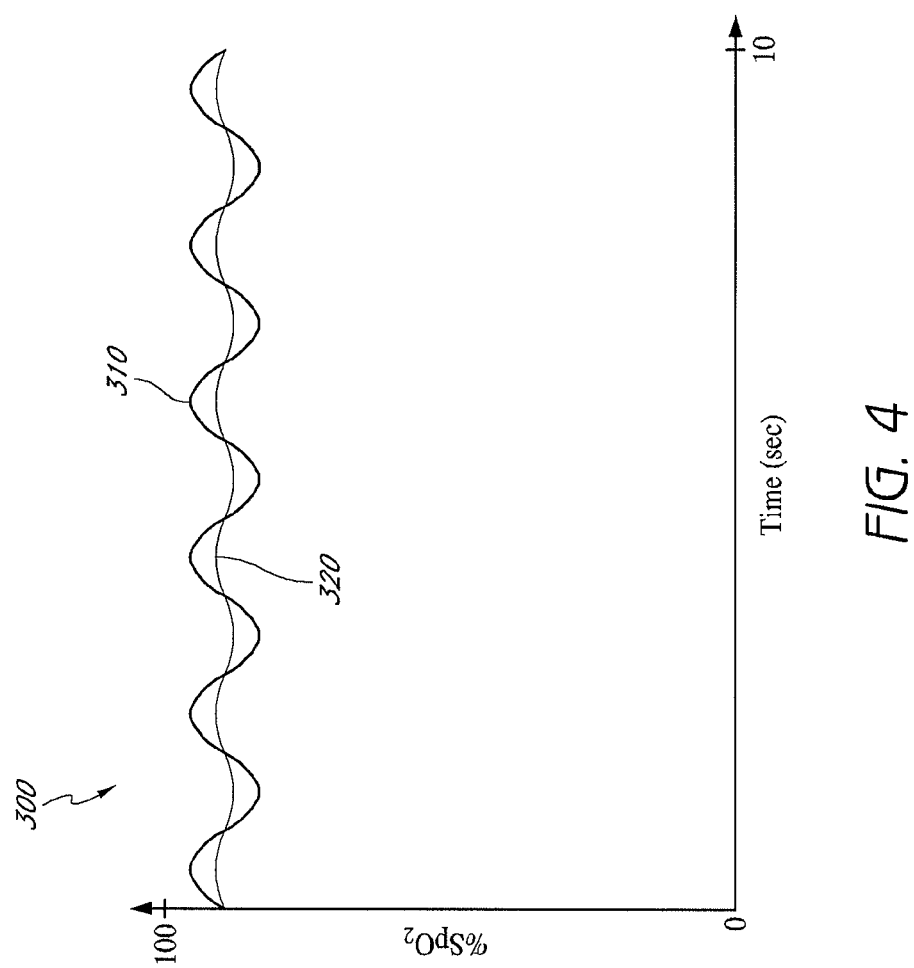
FIG. 4 illustrates variability of example $SpO_2$ oxygen saturation waveforms.

FIG. 4 illustrates an example graph 300 that plots oxygen saturation values over time for a patient receiving ventilation. The graph 300 plots an illustrative signal 310 with a relatively higher amplitude of difference and an illustrative signal 320 with a relatively lower amplitude of differences between high and low values over a respiratory cycle. These plots 310, 320 could be output, for example, by a physiological monitor as oxygen saturation graphs.

The signal 310 with higher amplitude of differences between maximum and minimum values of oxygen saturation over a respiratory cycle can reflect a stressed condition of the patient's lungs, caused by ventilation that is too extreme. In response to observing the high amplitude of the differences between the high and low values in the signal 310, a care giver could adjust ventilator parameters as described above. In response, the care giver could adjust the ventilation parameters as needed to maintain a lower amplitude of differences in the signal 320.

In an embodiment, one ventilation parameter a caregiver may monitor and adjust to maintain a desired amplitude of the differences in the percentage of oxygen saturation over a respiratory cycle or cycles is the fraction of inspired oxygen (FiO$_2$). The gases provided to the patient through a ventilator 150 (ventilation gases) may be composed of the types and percentages of gases found in ambient air, or may have different amounts of types of gases. For example, the percentage of oxygen a patient breathes in through a ventilator may be called the fraction of inspired oxygen, or FiO$_2$. Specifically, increased FiO$_2$ may be administered in order to maintain a patient's oxygen saturation within certain ranges.

In order for a caregiver to maintain adequate oxygen saturation by maintaining an appropriate FiO$_2$ to a patient, the oxygen saturation can be monitored according to the methods disclosed herein and the FiO$_2$ can be adjusted accordingly.

Figure 5:
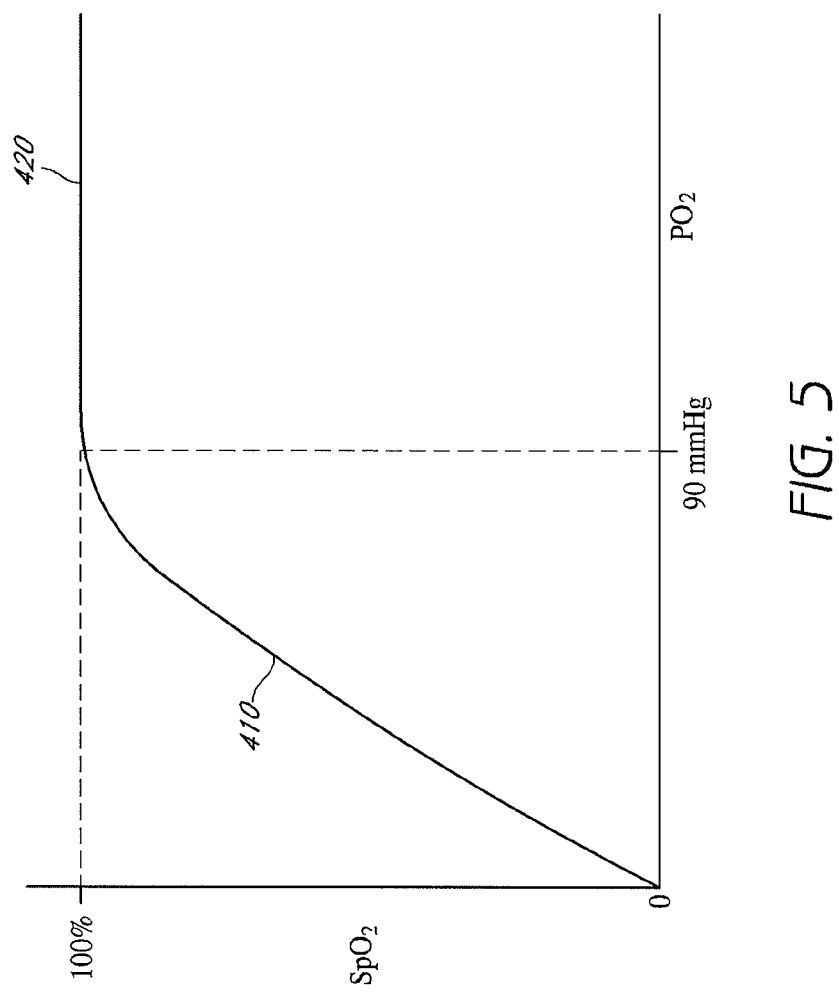
FIG. 5 illustrates a graph of $SpO_2$ versus the partial pressure of oxygen dissolved in the blood, $PO_2$.

FIG. 5 illustrates a graph of SpO$_2$ versus the partial pressure of oxygen dissolved in the blood, PO$_2$. This graph illustrates the relationship between the percentage of hemoglobin in the blood bound to oxygen to the partial pressure of oxygen dissolved in the blood. As the partial pressure of oxygen in the blood increases the increase the percentage of oxygen saturation of the hemoglobin will increase.

When the partial pressure of oxygen in the blood reaches about 90 mmHg, the oxygen saturation of the hemoglobin will plateau at 100 percent oxygen saturation. If the partial pressure of oxygen in the blood is increased to about 90 mmHg, the oxygen saturation will stay 100 percent saturated, and will not increase as no more oxygen may bind to the hemoglobin. This leaves a large range of partial pressures of oxygen dissolved in the blood that will result in an oxygen saturation of the hemoglobin at 100 percent. Therefore, this illustrates that the partial pressure of oxygen in the blood will affect the oxygen saturation of the hemoglobin.

Therefore, a caregiver may control the partial pressure of oxygen in the blood in order to manipulate or control the oxygen saturation of the hemoglobin. One way to do this is to manipulate the FiO$_2$ or fraction of inspired oxygen to a patient. When a caregiver increases the fraction of inspired oxygen to a patient, the partial pressure of oxygen in the alveolar sacs will increase. This will cause more of the oxygen in the lungs to be dissolved into the blood of the arteries, which may or may not bind to hemoglobin, depending on the SpO$_2$ level. Similarly, if a caregiver decreases the fraction of inspired oxygen the partial pressure of oxygen in the blood will decrease.

A caregiver may only change or manipulate the SpO$_2$ or oxygen saturation of the hemoglobin, if the partial pressure of oxygen is low enough so that the oxygen saturation is less than 100 percent saturated. Otherwise if the SpO$_2$ is 100 percent, and the partial pressure of the oxygen in a patient's blood is on the flat portion of the graph marked 420, changes in the partial pressure of oxygen dissolved in the blood will have no effect on the SpO$_2$ and therefore changes in the FiO$_2$ or the fraction of oxygen inspired by a patient will not effect or change the level of SpO$_2$. Similarly if the patient's PO$_2$ is in the range marked 420, the patient's SpO$_2$ will remain constant, and therefore changes in the SpO$_2$ due to the respiratory cycle (or other non-FiO$_2$ related changes) will not be observable.

Therefore, in order to utilize FiO$_2$ to control SpO$_2$ the FiO$_2$ must be decreased until the SpO$_2$ levels fall below 100 percent. This will place the SpO$_2$ on the portion of the graph marked 410 where changes in the FiO$_2$ will produce changes in the SpO$_2$ of a patient. This will allow a caregiver to monitor the changes in the SpO$_2$ levels and adjust the levels by changing the FiO$_2$ that is delivered to a patient.

In an embodiment, in order limit the amplitude in the difference of the SpO$_2$ over the course of the respiration cycle, it may be advantageous to control the FiO$_2$ delivered to a patient on the ventilator 150 so that it corresponds or stays within the range of the FiO$_2$ values on the part of the slope of the graph marked 410 in FIG. 5. In order to do this, the FiO$_2$ could begin at a value that provides an SpO$_2$ value of or near 100 percent generally within the range of the graph marked 420. Next, the FiO$_2$ could be lowered until the SpO$_2$ falls within a range known by persons of skill in the art to be on the part of the curve marked 410, while still providing a safe and adequate blood oxygenation level. Thereafter, a servo mechanism could raise the FiO$_2$ when it begins to decrease further, and lower the FiO$_2$ as soon as it begins to increase and then again raise the FiO$_2$ as soon as the SpO$_2$ begins to decrease, and so on. In another embodiment, other controls known in the art may keep the $SpO_2$ within a range that corresponds to a portion of the curve marked 410 by controlling the $FiO_2$ through any mechanisms or controls known in the art. In an embodiment, this range may be between 80-99, 85-99, 91-99, 91-97, 92-98, 93-97, 92-99, 95-97, or 96-97 percent $SpO_2$ or any other percentages of $SpO_2$ known in the art to be safe and withing the portion of the curve marked as 410 in FIG. 5.

FIG. 1 illustrates an embodiment of a physiological monitor 120 set up to provide an optimal $FiO_2$ to a patient. The ventilator 150 provides ventilation gas to the patient and can vary the $FiO_2$ of the ventilation gas provided to the patient. In an embodiment, the ventilator 150 may also be connected to the physiological monitor 120. In an embodiment, the physiological monitor 120 could provide information regarding the oxygen saturation or $SpO_2$ detected from the patient and send to the ventilator 150 to determine whether the $FiO_2$ should be increased or decreased or held constant. In another embodiment, the physiological monitor 120 could determine, based on the oxygen saturation or $SpO_2$, whether the $FiO_2$ should be increased or decreased or held constant and send a corresponding command signal through the control 126 to the ventilator 150. In an embodiment, the command signal could be a simple data message indicating the amount the $FiO_2$ should be increased or decreased.

Additional embodiments of using pulse oximetry to adjust ventilator parameters are described in the attached Appendices, which is to be considered a part of this application.

Conditional language used herein, such as, among others, "can," "could," "might," "may," "e.g.," and the like, unless specifically stated otherwise, or otherwise understood within the context as used, is generally intended to convey that certain embodiments may include, while other embodiments may not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Depending on the embodiment, certain acts, events, or functions of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

While the above detailed description has shown, described, and pointed out novel features as applied to various embodiments, it will be understood that various omissions, substitutions, and changes in the form and details of the device or process illustrated may be made without departing from the spirit of the disclosure. As will be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A noninvasive method of analyzing oxygen saturation of a patient, the method comprising:
   deriving oxygen saturation values from a patient, the oxygen saturation values reflecting oxygen saturation of blood at a tissue site over a respiration cycle of the patient;
   calculating a difference between a maximum and a minimum of the derived oxygen saturation values over the respiration cycle;
   outputting an indication of the difference between the maximum and the minimum of the derived oxygen saturation values; and
   outputting an indication of a risk of overextension of alveoli of the patient.

2. The method of claim 1, wherein said outputting the indication of the difference comprises outputting a graph of the difference between the maximum and the minimum of the derived oxygen saturation values.

3. The method of claim 1, wherein said outputting the indication of the difference comprises outputting a percentage value of variability.

4. The method of claim 1, further comprising determining whether the difference between the maximum and minimum of the derived oxygen saturation values is above a threshold value.

5. The method of claim 4, wherein said outputting the indication of the difference comprises generating an alarm in response to a variability being above the threshold value.

6. The method of claim 1, further comprising providing a control signal to a ventilator responsive to the difference between the maximum and minimum of the derived oxygen saturation values.

7. The method of claim 6, wherein the control signal to the ventilator increases or decreases an $FiO_2$ amount delivered by the ventilator to the patient.

8. The method of claim 7, wherein the $FiO_2$ amount is increased or decreased to keep the patient's oxygen saturation values on a steep part of a $SpO_2$ versus $FiO_2$ curve of the patient.

9. A physiological monitoring system, the system comprising:
   a physiological monitor comprising one or more processors configured to:
      derive oxygen saturation values from a patient, the oxygen saturation values corresponding to values of oxygen saturation in blood at a tissue site over a respiration cycle of the patient;
      calculate a difference between a maximum and a minimum of the derived oxygen saturation values over the respiration cycle;
      output an indication of the difference between the maximum and the minimum of the derived oxygen saturation values; and
      output an indication of a risk of overextension of alveoli of the patient.

10. The system of claim 9, wherein the physiological monitor is further configured to output the indication of the difference by at least outputting a graph of the difference between the maximum and the minimum of the derived oxygen saturation values.

11. The system of claim 9, wherein the physiological monitor is further configured to output the indication of the difference by at least outputting a percentage value representing the difference.

12. The system of claim 9, wherein the physiological monitor is further configured to determine whether the difference between the maximum and minimum of the derived oxygen saturation values is above a threshold value.

13. The system of claim 12, wherein the physiological monitor is further configured to output the indication of the difference by at least generating an alarm in response to the difference being above the threshold value.

14. The system of claim 9, wherein the physiological monitor is further configured to provide a control signal to a ventilator responsive to the difference between the maximum and minimum of the derived oxygen saturation values.

15. The system of claim 14, wherein the control signal to a ventilator increases or decreases an $FiO_2$ amount delivered to the patient.

16. The system of claim 15, wherein the $FiO_2$ amount is increased or decreased to keep the patient's oxygen saturation values on a steep part of a $SpO_2$ versus $FiO_2$ curve of the patient.

17. The system of claim 9, wherein the physiological monitor is further configured to derive the oxygen saturation values from a physiological signal obtained by a noninvasive optical sensor.

* * * * *

UNITED STATES PATENT AND TRADEMARK OFFICE
CERTIFICATE OF CORRECTION

| | | |
|---|---|---|
| PATENT NO. | : 8,670,811 B2 | Page 1 of 1 |
| APPLICATION NO. | : 12/824087 | |
| DATED | : March 11, 2014 | |
| INVENTOR(S) | : O'Reilly | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this
First Day of September, 2015

Michelle K. Lee
*Director of the United States Patent and Trademark Office*